(12) United States Patent
Shen et al.

(10) Patent No.: US 9,770,485 B2
(45) Date of Patent: Sep. 26, 2017

(54) METHODS FOR RESCUING LEARNING AND/OR MEMORY DEFICITS CAUSED BY ALZHEIMER'S DISEASE BY G-CSF

(75) Inventors: Che-Kun James Shen, Taipei (TW); Kuen-jer Tsai, Kaohsiung (TW)

(73) Assignee: Academia Sinica, Taipei (TW)

( * ) Notice: Subject to any disclaimer, the term of this patent is extended or adjusted under 35 U.S.C. 154(b) by 1215 days.

(21) Appl. No.: 12/510,387

(22) Filed: Jul. 28, 2009

(65) Prior Publication Data
US 2009/0317366 A1 Dec. 24, 2009

Related U.S. Application Data

(63) Continuation-in-part of application No. 11/358,392, filed on Feb. 21, 2006, now abandoned.

(51) Int. Cl.

| A61K 38/00 | (2006.01) |
|---|---|
| A61K 38/18 | (2006.01) |
| C07K 14/475 | (2006.01) |
| C07K 14/48 | (2006.01) |
| A61K 38/19 | (2006.01) |
| A61K 35/28 | (2015.01) |

(52) U.S. Cl.
CPC ............ *A61K 38/193* (2013.01); *A61K 35/28* (2013.01); *A01K 2207/10* (2013.01); *A01K 2267/0312* (2013.01)

(58) Field of Classification Search
CPC ........... A61K 2300/00; A61K 38/1793; G01N 2800/2821; G01N 33/6896; G01N 2800/28; C07K 16/243
See application file for complete search history.

(56) References Cited

U.S. PATENT DOCUMENTS

| 7,598,049 | B2 * | 10/2009 | Ray et al. .................... 435/7.21 |
|---|---|---|---|
| 7,723,302 | B2 | 5/2010 | Wu et al. |
| 8,398,972 | B2 * | 3/2013 | Bebbington et al. ...... 424/130.1 |
| 2002/0198150 | A1 | 12/2002 | Chajut |
| 2003/0170237 | A1 | 9/2003 | Ni et al. |
| 2004/0141946 | A1 | 7/2004 | Schaebitz |
| 2005/0221348 | A1 * | 10/2005 | Ray et al. ..................... 435/6 |
| 2006/0094064 | A1 * | 5/2006 | Ray et al. ..................... 435/7.2 |
| 2006/0153772 | A1 * | 7/2006 | Jacobsen ..................... 424/9.2 |
| 2006/0153799 | A1 | 7/2006 | Zhao et al. |
| 2007/0037200 | A1 * | 2/2007 | Ray et al. ..................... 435/6 |

FOREIGN PATENT DOCUMENTS

| JP | 5246885 | 9/1993 | |
|---|---|---|---|
| WO | WO2008/036374 | * 3/2008 | .............. A61K 35/30 |

OTHER PUBLICATIONS

Martin Sarter, "Animal Cognition: Defining the Issues," Neuroscience and Biobehavioral Reviews, 28:645-650 (2004).
Burgess et al. J of Cell Bio. 111:2129-2138 (1990).
Bowie et al. Science 247:1306-1310 (1990).
Anger. Neurotoxicology 12:403-413 (1991).
Tayebati. Mech. Ageing Dev. 127:100-108 (2006).
Sarter. Neurosci. and Biobehav. Rev. 28:645-650 (2004).
Stedman's Medical Dictionary, 27th Edition, The Definition of "Prophylactic" and the definition of "therapeutic".
The Definition of Cognition and Cognitive Ability on Answers.com/topic.cognition [retrieved Mar. 7, 2007].
Pawson et al. Science 300:445-452 (2003).
Tsai et al "G-CSF rescues the memory impairment of animal models of Alzheimer's disease" JEM vol. 204, Jun. 11, 2007.
Diederich et al. "The Role of Granulocyte-Colony Stimulating Factor (G-CSF) in the Healthy Brain: A Characterization of G-CSF-Deficient Mice" The Journal of Neuroscience, Sep. 16, 2009 • 29(37):11572-11581.
Nancy R. Gough "Stimulating Neurogenesis to Treat Alzheimer's Disease" Sci. STKE, Jun. 19, 2007 vol. 2007, Issue 391, p. tw213.
Alzheimer Research Forum,"A Blood Test for AD?" Nature Medicine, published on Oct. 15, 2007, http://www.alzforum.org/new/detailprint.asp?id=1670.
Sanchez-Ramos et al "Granulocyte colony stimulating factor decreases brain amyloid burden and reverses cognitive impairment in Alzheimer's mice" Neuroscience. Sep. 29, 2009;163(1):55-72. Epub Jun. 14, 2009.
Wang et al "Apocynin protects against global cerebral ischemia—reperfusion-induced oxidative stress and injury in the gerbil hippocampus" BRAINRESEARCH1090 (2006) 182-189.
Tarkowski E et al "Local and systemic GM-CSF increase in Alzheimer's disease and vascular dementia" Acta Neurol Scand. Mar. 2001;103(3):166-74.

\* cited by examiner

*Primary Examiner* — Chang-Yu Wang
(74) *Attorney, Agent, or Firm* — Hsiu-Ming Saunders; Intellectual Property Connections, Inc.

(57) ABSTRACT

A method for treating a progressive neurodegenerative disorder with bone marrow stem cells and a G-CSF receptor agonist.

15 Claims, No Drawings

SEQUENCE LISTING

```
<160> NUMBER OF SEQ ID NOS: 1

<210> SEQ ID NO 1
<211> LENGTH: 174
<212> TYPE: PRT
<213> ORGANISM: Homo sapiens

<400> SEQUENCE: 1

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

METHODS FOR RESCUING LEARNING AND/OR MEMORY DEFICITS CAUSED BY ALZHEIMER'S DISEASE BY G-CSF

CROSS-REFERENCE TO RELATED APPLICATION

The present application is a continuation-in-part application of U.S. patent application Ser. No. 11/358,392, filed on Feb. 21, 2006, which status is abandoned, the content of which is hereby incorporated by reference in its entirety.

BACKGROUND

Progressive neurodegenerative disorders (PNDs), exemplified by Alzheimer's disease, cause a slow but inexorable loss of neurons that is accompanied by degrading cognitive or motor function and is followed by death of the afflicted individual. The effects of PNDs are devastating to the quality of life of those afflicted as well as that of their families. Moreover, PNDs impose an enormous health care burden on society. Indeed, as this class of diseases primarily affects the expanding elderly population, their prevalence and societal impact are expected to become even more severe in the coming years.

One of the most promising therapeutic approaches for treating PNDs is neuronal replacement with transplanted neurons derived from stem cells, which are found scattered throughout various tissues of the adult human body in very small numbers. Human embryonic stem cells (HESCs) are the most well characterized for potential therapeutic applications. Unfortunately, the development of HESC lines in sufficient quantity and of adequate quality for clinical applications has been severely hampered by controversy over their embryonic origin. However, even if clinical-grade HESC lines do become readily available, transplanting in vitro-differentiated, HESC-derived neurons is risky and requires highly invasive intracerebral injection of the neurons into a patient. Thus, there is an urgent and ongoing need for methods that afford low risk, non-invasive replenishment of neurons for treating PNDs or inhibiting their onset.

SUMMARY

The present invention is based, in part, on the finding that granulocyte-colony stimulating factor (G-CSF), in combination with bone marrow stem cells, promotes neurogenesis.

Accordingly, this invention features a method of treating a progressive neurodegenerative disorder ("PND") by transplanting to a subject in need thereof bone marrow stem cells (e.g., autologous bone marrow stem cells) and subsequently administering to the subject an effective amount of G-CSF. The G-CSF can be administered systemically (e.g., subcutaneously). Examples of PND include Alzheimer's disease, Parkinson's disease, Huntington's disease, Lewy body dementia, and Pick's disease.

The term "PND" as used herein refers to any condition that leads to neuronal cell death over a period greater than 3 days (e.g., one month or 20 years) and are behaviorally manifested as abnormal and worsening cognitive abilities or motor functions in an afflicted subject. PNDs include those that decrease a cognitive ability (e.g., short term memory, long term memory, spatial orientation, face recognition, or language ability). Some PNDs result from hippocampal neurodegeneration (at least in part). Some examples of a PND are Alzheimer's disease, Parkinson's disease, Huntington's disease, Lewy body dementia, or Pick's disease. Of note, some PNDs affect both cognitive abilities and motor functions (e.g., Huntington's disease). In one example of the invention, the PND is Alzheimer's disease.

Other features or advantages of the present invention will be apparent from the following detailed description, and also from the claims.

DETAILED DESCRIPTION

We have found that G-CSF promotes migration to the brain of bone marrow stem cells transplanted into a subject and that, once in the brain, the stem cells differentiated into neuron cells, resulting in neurogenesis.

Accordingly, within the scope of this invention is a method for treating a PND by transplanting bone marrow stem cells to a PND patient (e.g., a human patient) and then administering to that patient an effective amount of G-CSF, which is a G-CSF receptor (G-CSFR) agonist, i.e., a compound that activates the G-CSF/G-CSFR signaling pathway.

The bone marrow cells used in this method of this invention can be obtained from a suitable donor (e.g., a healthy human whose HLA type matches that of the patient). They also can be derived from the patient. Techniques for obtaining bone marrow stem cells, enriching/culturing bone marrow stem cells in vitro, and conducting bone marrow stem cell transplantation are well known in the art.

A G-CSFR agonist can be a purified mammalian polypeptide that includes the amino acid sequence of a mature mammalian G-CSF (e.g., human, mouse, or rat G-CSF), namely, one that does not include a signal peptide sequence. For example, the G-CSFR agonist can include amino acids 13-186 of human G-CSF (GenBank Accession No. AAA03056):

```
                                          (SEQ ID NO: 1)
TPLGPASSLPQSFLLKCLEQVRKIQGDGAALQEKLCATYKLCHPEELVLL

GHSLGIPWAPLSSCPSQALQLAGCLSQLHSGLFLYQGLLQALEGISPELG

PTLDTLQLDVADFATTIWQQMEELGMAPALQPTQGAMPAFASAFQRRAGG

VLVASHLQSFLEVSYRVLRHLAQP
```

A mammalian G-CSF or G-CSF-containing polypeptide can be purified using standard techniques from a native source (e.g., a cell line that secretes native G-CSF) or a recombinant expression source (e.g., E. coli, Yeast, insect cells, or mammalian cells that express transgenic G-CSF). Recombinant human G-CSF can also be purchased from a commercial source, e.g., Amgen Biologicals (Thousand Oaks, Calif.). Alternatively, recombinant G-CSF can be purified as described in, e.g., U.S. Pat. No. 5,849,883.

In addition to G-CSF, a G-CSFR agonist can also be a G-CSF sequence variant (as described in, e.g., U.S. Pat. Nos. 6,358,505 and 6,632,426) that is at least 70% identical to SEQ ID NO:1 (i.e., having any percent identity between 70% and 100%). In general, G-CSF sequence variations should not alter residues critical to G-CSF function, including (in human G-CSF) residues K16, E19, Q20, R22, K23, D27, D109, and F144. See, e.g., Young et al., id. and also U.S. Pat. No. 6,358,505, example 29.

When comparing a G-CSF sequence with that of a sequence variant, the percent identity between the two sequences is a function of the number of identical positions shared by the sequences, taking into account the number of gaps, and the length of each gap, which need to be introduced for optimal alignment of the two sequences. The comparison of sequences and determination of percent identity between two sequences can be accomplished using a mathematical algorithm. The percent identity between two amino acid sequences can be determined using the Needleman and Wunsch (1970), *J. Mol. Biol.* 48:444-453, algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The G-CSFR agonist can be a chemically modified mammalian G-CSF, e.g., one having a linked polyethylene glycol moiety as described in U.S. Pat. No. 5,824,778.

Alternatively, the G-CSFR agonist can be a monoclonal antibody or antibody-derived molecule (e.g., an Fab fragment) that binds to and activates a G-CSFR as described in, e.g., U.S. Patent Application No. 20030170237.

Preferably, the G-CSFR agonist has a 50% effective concentration (EC50) no greater than about ten times that of G-CSF. In addition, the affinity of the G-CSFR agonist should be no less than about one tenth that of G-CSF. Assays for determining G-CSFR agonist properties are described in detail in, e.g., Young et al. (1997), *Protein Science* 6:1228-1236 and U.S. Pat. No. 6,790,628. Moreover, such assays can be used to identify entirely novel G-CSFR agonists (e.g., small molecule agonists) that meet the above-mentioned criteria.

The above-described G-CSFR agonists can be used to treat a subject suffering from a PND that decreases a cognitive ability. Examples of PNDs that affect at least one cognitive ability include but are not limited to AD, Parkinson's disease, Huntington's disease, Lewy body Dementia, or Pick's disease. The PND is treated by systemically administering to an afflicted subject a composition containing an effective amount of one the above-described G-CSFR agonists. Prior to administration of the inhibitor composition, the subject can be diagnosed as suffering from a PND. In the case of a disorder that affects a cognitive ability, a subject can be diagnosed by any one of a number of standardized cognitive assays, e.g., the Mini-Mental State Examination, the Blessed Information Memory Concentration assay, or the Functional Activity Questionnaire. See, e.g., Adelman et al. (2005), *Am. Family Physician*, 71(9): 1745-1750. Indeed, in some cases a subject can also be diagnosed as having a high risk of developing a PND, even in the absence of overt symptoms. For example, the risk of Alzheimer's disease in a subject can be determined by detecting a decrease in the volumes of the subject's hippocampus and amygdale, using magnetic resonance imaging. See, e.g., den Heijer et al. (2006), *Arch. Gen. Psychiatry*, 63(1):57-62. Accordingly, the subject's risk of a PND can be reduced by prophylactically administering to the subject a composition containing an effective amount of a G-CSFR agonist.

G-CSFR agonists of high efficacy for treating a PND can be selected based on their evaluation in a non-human mammal suffering from a PND. The G-CSFR agonist to be tested is systemically administered to a test mammal suffering from a PND known to impair performance of a behavioral task. The test mammal's performance of the task is then assessed and compared to that of a control mammal suffering from the same PND, but not administered the G-CSFR agonist. A better performance by the test mammal indicates that the G-CSFR agonist has high efficacy for treating the PND.

The non-human mammals used in the behavioral task can be, e.g., rodents such as mice, rats, or guinea pigs. Non-rodent species can also be used, e.g., rabbits, cats, or monkeys. In some cases, the non-human mammals are genetically modified to develop a PND. For example they can express a transgene or have suppressed expression of a native gene. Expression of the transgene or suppression of the native gene can be temporally or regionally regulated. Methods for transgene expression and gene suppression as well as their spatial and temporal control in non-human mammals (e.g., in mice and other rodents) are well established. See, e.g, Si-Hoe et al. (2001), *Mol. Biotechnol.*, 17(2):151-182; Ristevski (2005), *Mol. Biotechnol.*, 29(2): 153-163; and Deglon et al. (2005), *J. Gene Med.*, 7(5):530-539.

A number of transgenic mouse models of PNDs (e.g., Alzheimer's disease, and amylotrophic lateral sclerosis) have been established. See, e.g., Spires et al (2005), *NeuroRx.*, 2(3):447-64 and Wong et al. (2002), *Nat. Neurosci.*, 5(7):633-639. Such transgenic animal models spontaneously develop a PND that is manifested behaviorally by impaired learning, memory, or locomotion. Such animal models are suitable for selecting high efficacy G-CSFR agonists as described above.

A PND can also be induced in a non-human mammal by non-genetic means. For example, a PND that affects learning and memory can be induced in a rodent by injecting aggregated Aβ peptide intracereberally as described in, e.g., Yan et al. (2001), *Br. J. Pharmacol.*, 133(1):89-96.

Cognitive abilities, as well as motor functions in non-human animals suffering from a PND, can be assessed using a number of behavioral tasks. Well-established sensitive learning and memory assays include the Morris Water Maze (MWM), context-dependent fear conditioning, cued-fear conditioning, and context-dependent discrimination. See, e.g., Anger (1991), *Neurotoxicology*, 12(3):403-413. Examples of motor behavior/function assays, include the rotorod test, treadmill running, and general assessment of locomotion.

The above-mentioned G-CSFR agonists can be incorporated into pharmaceutical compositions for prophylactic or therapeutic use. For example, a pharmaceutical composition can include an effective amount of recombinant human G-CSF and a pharmaceutically acceptable carrier. The term "an effective amount" refers to the amount of an active composition that is required to confer a prophylactic or therapeutic effect on the treated subject. Generally, the effective dose will result in a circulating G-CSFR agonist concentration sufficient to reliably increase the numbers of hemapoietic progenitor cells in circulating blood. Nonetheless, effective doses will vary, as recognized by those skilled in the art, depending on the types of PNDs treated and their severity, the stage of intervention, the general health or age of the subject, previous treatments, route of administration, excipient usage, and the possibility of co-usage with other prophylactic or therapeutic treatment.

To practice the methods of the present invention, a G-CSFR agonist-containing composition can be administered systemically via a parenteral or rectal route. The term "parenteral" as used herein refers to subcutaneous, intracutaneous, intravenous, intramuscular, intra-articular, intra-arterial, intrasynovial, intrasternal, intrathecal, or intralesional, as well as any suitable infusion technique.

When administered, the therapeutic composition is preferably in the form of a pyrogen-free, parenterally acceptable aqueous solution. The preparation of such a parenterally acceptable protein solution, having due regard to pH, isotonicity, stability and the like, is within the skill of the art. Among the parentarally acceptable vehicles and solvents that can be employed are mannitol, water, Ringer's solution, and isotonic sodium chloride solution.

As PNDs are chronic conditions, continuous systemic administration is useful for treating an afflicted subject. Methods for continually infusing a composition and sustaining its systemic concentration over time are known in the art. For example, the compositions described herein can be released or delivered from an osmotic mini-pump or other time-release device. The release rate from an elementary osmotic mini-pump can be modulated with a microporous, fast-response gel disposed in the release orifice. An osmotic mini-pump is useful for controlling release of the composition over an extended period of time (e.g., from one week to five months). Such mini pumps as well as other sustained release devices are available commercially from, e.g., DURECT corporation (Cupertino, Calif.). An active composition can also be administered in the form of suppositories for rectal administration.

The following specific example is to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1: Effect of G-CSF in Treating Alzheimer's Disease

An Alzheimer's disease-like PND was induced in mice by intraventricular injection of aggregated Aβ peptide as described in Yan et al., ibid.

Aggregated Aβ was prepared from solutions of 10 mM soluble $A\beta_{(1-42)}$ in 0.01 M phosphate-buffered saline, pH 7.4. Aβ peptide was purchased from Sigma-Aldrich (St. Louis, Mo.). The Aβ solution was then incubated at 37° C. for three days to form the aggregated Aβ and stored at −70° C. prior to use. Prior to injection of the aggregated Aβ, eight-week old C57BL/6 male mice were anesthetized by intraperitoneal administration of sodium pentobarbital (40 mg/kg). The aggregated Aβ was then stereotaxically injected into dorsal hippocampus and cortex bilaterally using a 26-gauge needle connected to a Hamilton microsyringe (Hamilton, Reno, Nev.). The injection volume of aggregated Aβ or phosphate buffered saline (PBS; a control solution) was one microliter. After the injection, the resulting PND was allowed to develop over a period of seven days before the mice were assessed for pathology or behavioral deficits. Brain immunohistochemistry was used to confirm that Aβ aggregates formed at the injected sites.

Spatial learning ability of the mice was assessed in the Morris water-maze learning task. The animals were subjected to four trials per session, and two sessions per day, with one session given in the morning and the other in the afternoon. A total of six sessions were given for evaluating the animals. In each of the four trials, the animals were randomly placed at four different starting positions equally spaced around the perimeter of a pool filled with water made opaque by addition of powdered milk. They were then allowed to search for a hidden platform under the surface of the pool. If an animal could not find the platform after 120 seconds, it was guided to the platform. After mounting the platform, the animals were allowed to stay there for 20 seconds. The time required for each animal to find the platform was recorded as the escape latency.

Aβ-treated mice were tested in the Morris water maze spatial learning task and their performance was compared to that of control mice injected with PBS alone. The performance of the Aβ-treated mice was significantly worse than that of the control mice, as demonstrated by a significantly higher escape latency.

Subsequently, the Aβ-treated mice were divided into a G-CSF group and a control control group. Mice in the G-CSF group were injected subcutaneously with recombinant human G-CSF (Amgen Biologicals) at a dose (50 μg/kg) once daily for five days. In parallel, mice in the control group were injected subcutaneously with PBS. Afterwards, the mice from both groups were tested in the water maze task and their performance was compared with that of mice treated with either G-CSF or PBS alone.

Aβ-treated mice in the G-CSF group were found to perform this task significantly better than the mice in the Aβ-treated control group, as demonstrated by an escape latency similar to that of mice treated with either G-CSF or PBS alone.

Consistent with the behavioral rescue by G-CSF, neurogenesis, as assessed by BrdU (a marker of cell proliferation) plus MAP2 (a neuron-specific marker) co-labeling of new neurons, was found to be higher in the cortex and hippocampus of Aβ-treated animals that were administered G-CSF versus the same areas in Aβ-treated animals administered only PBS.

These studies indicated that systemically administered G-CSF could rescue behavioral deficits caused by intracerebral injection of aggregated Aβ and stimulated increased neurogenesis in the injected regions.

Example 2: G-CSF Promotes Migration of Transplanted Bone Marrow Stem Cells to Brain Transgenic mice Tg2576, over-expressing amyloid precursor protein (APP), were crossed with transgenic mice expressing green fluorescent protein (GFP). Two special lines were generated: $APP^+/GFP^+$ and $APP^+/GFP^-$. Bone marrow cells were isolated from the thighbones of $APP^+/GFP^+$ mice (donors) and transplanted into lethally irradiated $APP^+/GFP^-$ mice (receivers) from tail veins.

Twelve weeks after transplantation, G-CSF (50 μg/kg) was injected into the receiver mice subcutaneously once per day for 5 days, following the conditions described in Tsai et al., 2007, *Proceedings of the National Academy of Science USA* 99:3990-3995. The brain sections from both the treated and untreated receiver mice were then analyzed by immunohistochemistry.

$GFP^+$ cells were observed in the brains of the G-CSF-treated mice, particularly, in their hippocampus regions, but not in the brains of the untreated mice. This result indicates that G-CSF promoted migration of donor bone marrow cells, which are $GFP^+$, to the brain.

A double immunofluoresence-staining assay was employed to identify the locations of GFP and NeuN, a neuronal protein marker, in the brains of the G-CSF-treated receiving mice. Briefly, brain samples were obtained from the mice, sectioned, and subjected to immunostaining first with a rabbit polyclonal anti-Neu antibody (Chemicon) and then with a labeled secondary antibody specific to rabbit IgG, following routine procedures. The stained sections were analyzed by a Carl Zeiss LSM510 laser-scanning confocal microscope. The green (Alex488) and red (Alex555) fluorochromes on the stained samples were excited by laser beam at 488 nm and 543 nm, respectively.

A number of neuron cells, characterized as $NeuN^+$ cells, were $GFP^+$, indicating that they were differentiated from the $GFP^+$ bone marrow stem cells transplanted into the receiver mice. This result demonstrates that G-CSF promotes migration of bone marrow cells into the brain and the stem cells have then differentiated into neuron cells. It confirms that the combination of bone marrow stem cell transplantation and G-CSF administration is an effective approach in repairing neural damages and in treating neurodegenerative disorders.

From the above description, one skilled in the art can easily ascertain the essential characteristics of the present invention, and without departing from the spirit and scope thereof, can make various changes and modifications of the invention to adapt it to various usages and conditions. Thus, other embodiments are also contemplated.

What is claimed is:

1. A method of rescuing learning and/or memory deficits caused by Alzheimer's disease, comprising:
   (a) administering to a subject suffering from the learning and/or memory deficits caused by the Alzheimer's disease granulocyte-colony stimulating factor (G-CSF) in an effective amount to rescue the learning and/or memory deficits caused by the Alzheimer's disease in the subject; and
   (b) testing the subject for learning and/or memory performance.

2. The method of claim 1, wherein the learning and/or memory performance comprises spatial learning ability.

3. The method of claim 1, wherein the subject suffering from the Alzheimer's disease is administered G-CSF daily.

4. The method of claim 3, wherein the subject suffering from Alzheimer's disease is administered G-CSF daily for no less than 5 days.

5. The method of claim 1, wherein the learning and/or memory performance of the subject administered with the G-CSF is improved compared with Alzheimer s disease subjects without administration of the G-CSF.

6. A method of rescuing spatial learning and/or memory deficits caused by Alzheimer's disease, comprising:
   administering to a subject suffering from the spatial learning and/or memory deficits caused by the Alzheimer's disease granulocyte-colony stimulating factor (G-CSF) in an effective amount to rescue the spatial learning and/or memory deficits caused by the Alzheimer's disease in the subject.

7. The method of claim 6, wherein the subject suffering from Alzheimer's disease is administered G-CSF daily.

8. The method of claim 7, wherein the subject suffering from Alzheimer's disease is administered G-CSF daily for no less than 5 days.

9. The method of claim 6, wherein the learning and/or memory performance of the subject administered with the G-CSF is improved compared with Alzheimer's disease subjects without administration of the G-CSF.

10. A method of rescuing learning and memory deficits caused by Alzheimer's disease in a subject in need thereof, comprising:

administering to the subject in need thereof granulocyte-colony stimulating factor (G-CSF) in an effective amount to rescue the learning and memory deficits in the subject.

11. The method of claim 10 further comprising:
testing the subject suffering from the Alzheimer's disease for learning and/or memory performance.

12. The method of claim 11, wherein the testing step comprises assessing spatial learning ability of the subject suffering from the Alzheimer's disease.

13. The method of claim 10, wherein the subject suffering from Alzheimer's disease is administered G-CSF daily.

14. The method of claim 13, wherein the subject suffering from Alzheimer's disease is administered G-CSF daily for no less than 5 days.

15. The method of claim 10, wherein the learning and/or memory performance of the subject administered with the G-CSF is improved compared with Alzheimers disease subjects without administration of the G-CSF.

* * * * *